(12) United States Patent
Hessler

(10) Patent No.: US 9,629,621 B2
(45) Date of Patent: Apr. 25, 2017

(54) ENDOSCOPIC PURSE STRING SURGICAL DEVICE

(71) Applicant: Covidien LP, Mansfield, MA (US)

(72) Inventor: Thomas R. Hessler, Bethel, CT (US)

(73) Assignee: Covidien LP, Mansfield, MA (US)

( * ) Notice: Subject to any disclaimer, the term of this patent is extended or adjusted under 35 U.S.C. 154(b) by 351 days.

(21) Appl. No.: 14/338,862

(22) Filed: Jul. 23, 2014

(65) Prior Publication Data
US 2014/0336677 A1    Nov. 13, 2014

Related U.S. Application Data

(63) Continuation of application No. 13/166,039, filed on Jun. 22, 2011, now Pat. No. 8,827,136.
(Continued)

(51) Int. Cl.
*A61B 17/072* (2006.01)
*A61B 17/04* (2006.01)
(Continued)

(52) U.S. Cl.
CPC ...... *A61B 17/0469* (2013.01); *A61B 17/0684* (2013.01); *A61B 17/072* (2013.01); *A61B 17/115* (2013.01); *A61B 17/00234* (2013.01); *A61B 2017/07214* (2013.01); *A61B 2017/1142* (2013.01)

(58) Field of Classification Search
CPC ... A61B 17/04; A61B 17/0469; A61B 17/072; A61B 17/07207; A61B 17/00234; A61B 17/0057; A61B 17/115; A61B 2017/07214

USPC .............. 227/19, 175.1, 175.2, 176.1, 180.1; 606/142, 144, 139, 153, 219
See application file for complete search history.

(56) References Cited

U.S. PATENT DOCUMENTS 4,345,600 A * 8/1982 Rothfuss ................ A61B 17/04
                                                     606/148
4,605,002 A    8/1986 Rebuffat
(Continued)

FOREIGN PATENT DOCUMENTS

| | | |
|---|---|---|
| EP | 0503662 A1 | 9/1992 |
| EP | 0641546 A1 | 3/1995 |
| WO | 9424947 A1 | 11/1994 |

OTHER PUBLICATIONS

Japanese Office Action dated Apr. 30, 2015, issued in Japanese Application No. 2011-165851.
(Continued)

*Primary Examiner* — Scott A. Smith

(57) ABSTRACT

An endoscopic surgical stapler for applying a suture to tissue including an elongated tubular member, a first jaw positioned at the distal end portion of the tubular member and having a longitudinal axis, and a second jaw disposed in substantially parallel relation to the first jaw at the distal end portion of the tubular member. The second jaw is movable in a direction substantially perpendicular to its longitudinal axis toward the first jaw, while maintaining the substantially parallel relation between the first and second jaws. A stapling assembly is disposed in each of the first and second jaws and configured to apply surgical staples to the tissue such that a suture, in combination with the surgical staples, forms a purse string with the tissue when the surgical stapler is activated.

19 Claims, 14 Drawing Sheets

Related U.S. Application Data

(60) Provisional application No. 61/372,610, filed on Aug. 11, 2010.

(51) Int. Cl.
  *A61B 17/115* (2006.01)
  *A61B 17/068* (2006.01)
  *A61B 17/00* (2006.01)
  *A61B 17/11* (2006.01)

(56) References Cited

U.S. PATENT DOCUMENTS

| | | | |
|---|---|---|---|
| 4,749,114 A | 6/1988 | Green | |
| 4,773,420 A | 9/1988 | Green | |
| 4,821,939 A | 4/1989 | Green | |
| 4,915,107 A * | 4/1990 | Rebuffat | A61B 17/0469 606/144 |
| 5,188,636 A | 2/1993 | Fedotov | |
| 5,242,457 A | 9/1993 | Akopov et al. | |
| 5,389,098 A * | 2/1995 | Tsuruta | A61B 17/00234 606/142 |
| 5,425,737 A | 6/1995 | Burbank et al. | |
| 5,484,451 A | 1/1996 | Akopov et al. | |
| 5,490,856 A | 2/1996 | Person et al. | |
| 5,540,375 A | 7/1996 | Bolanos et al. | |
| 5,551,622 A * | 9/1996 | Yoon | A61B 17/072 227/176.1 |
| 5,573,543 A | 11/1996 | Akopov et al. | |
| 5,662,260 A | 9/1997 | Yoon | |
| 5,843,098 A | 12/1998 | Allen et al. | |
| 5,891,159 A | 4/1999 | Sherman et al. | |
| 5,911,728 A | 6/1999 | Sepetka et al. | |
| 6,315,183 B1 | 11/2001 | Piraka | |
| 6,716,232 B1 | 4/2004 | Vidal et al. | |
| 7,235,089 B1 * | 6/2007 | McGuckin, Jr. | A61B 17/00234 227/180.1 |
| 7,857,184 B2 | 12/2010 | Viola | |
| 7,942,303 B2 | 5/2011 | Shah | |
| 7,981,124 B2 * | 7/2011 | Brand | A61B 17/0469 606/144 |
| 8,827,136 B2 | 9/2014 | Hessler | |
| 2005/0177181 A1 * | 8/2005 | Kagan | A61B 17/00234 606/151 |
| 2007/0208360 A1 * | 9/2007 | Demarais | A61B 17/0057 606/153 |
| 2008/0249544 A1 | 10/2008 | Brand | |
| 2009/0048613 A1 | 2/2009 | Surti | |
| 2010/0249807 A1 | 9/2010 | Chen et al. | |
| 2010/0305609 A1 | 12/2010 | Cartledge et al. | |

OTHER PUBLICATIONS

Extended European Search Report dated Apr. 17, 2014 for EP 11 25 0716.

Japanese Office Action dated Dec. 19, 2014, issued in Japanese Appln. No. 2011-165851.

Japanese Office Action dated Jul. 16, 2015, issued in Japanese Application No. 2011-165851.

Japanese Office Action dated Sep. 30, 2016, issued in Japanese Application No. 2011-165851.

* cited by examiner

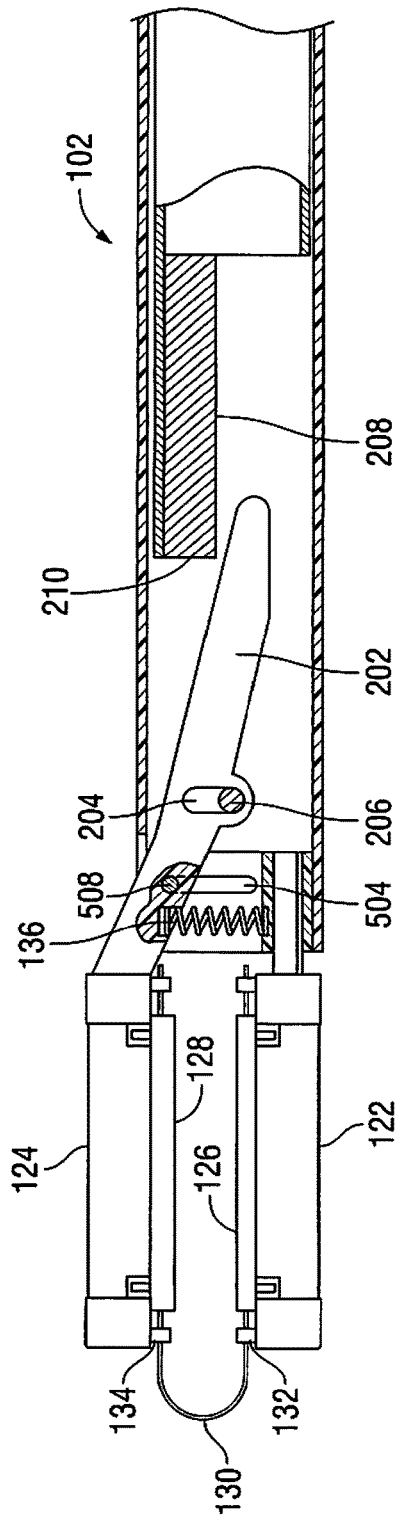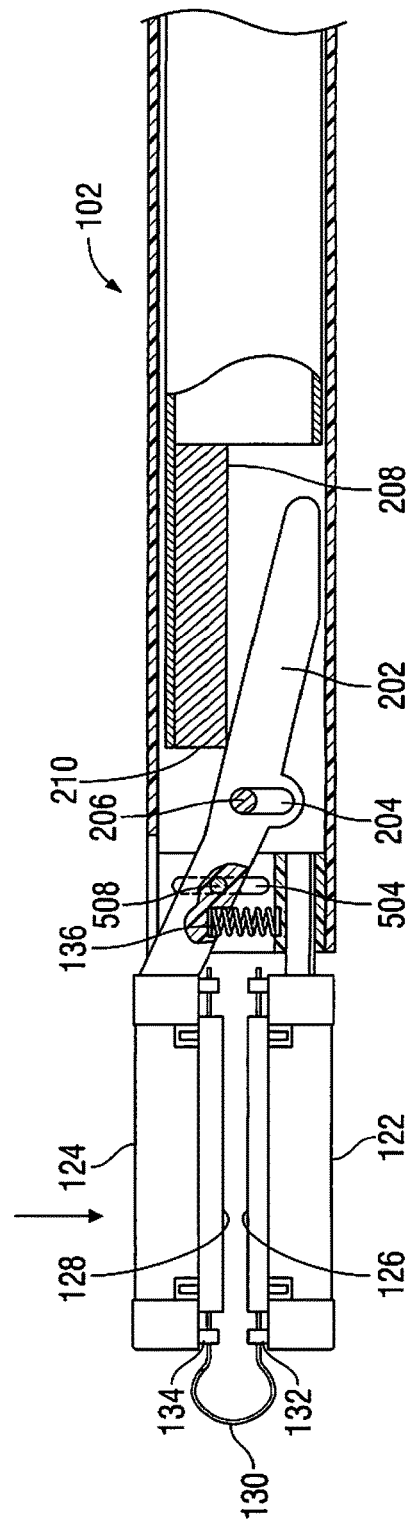

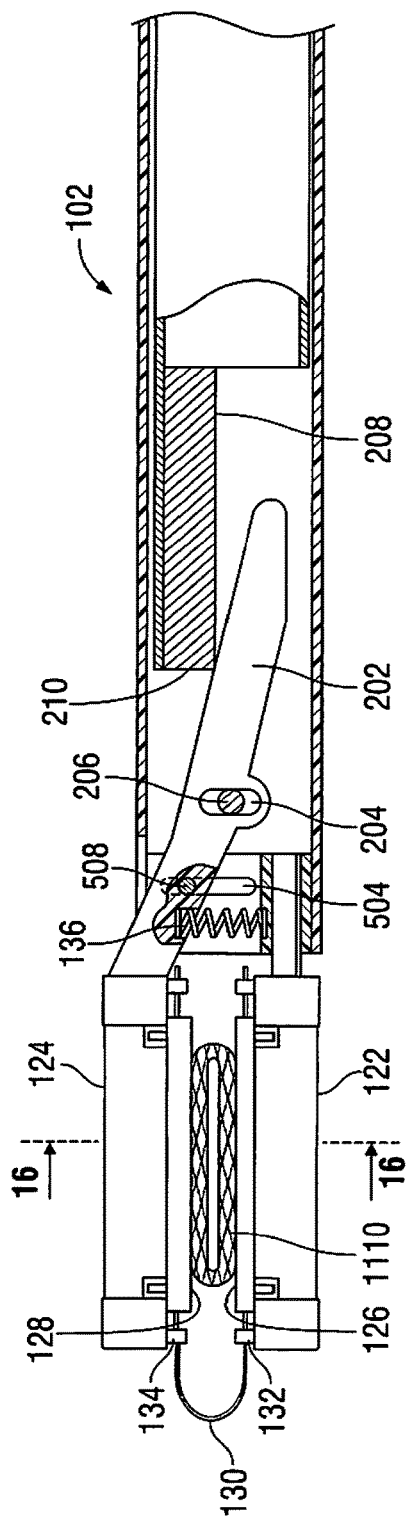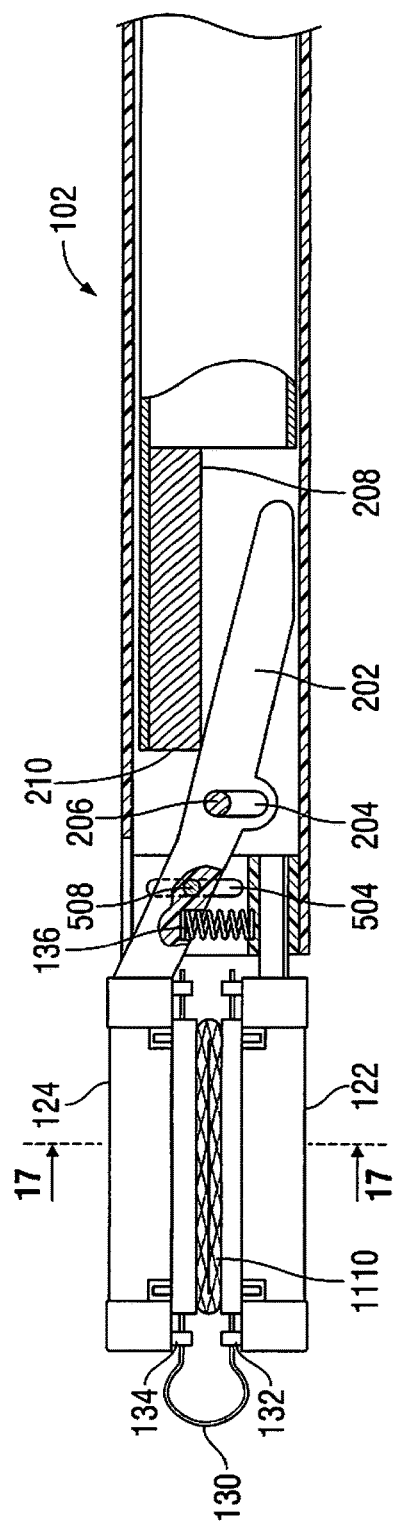

ENDOSCOPIC PURSE STRING SURGICAL DEVICE

CROSS-REFERENCE TO RELATED APPLICATIONS

This application is a Continuation of U.S. patent application Ser. No. 13/166,039 filed Jun. 22, 2011, now U.S. Pat. No. 8,827,136, which claims benefit of U.S. Provisional Application No. 61/372,610 filed Aug. 11, 2010, and the disclosures of each of the above-identified applications are hereby incorporated by reference in their entirety.

TECHNICAL FIELD

The present disclosure relates to a surgical stapler, and more particularly, to an endoscopic surgical stapler for affixing a purse string suture to tissue.

BACKGROUND OF RELATED ART

A circular stapler is one device that can be used in surgical applications for the joining of body tissue. In the area of surgical anastomotic stapling, it can be used for joining pieces of tissue in a manner such that a continuous pathway, lumen, or surgical opening, is formed after the tissue is stapled together. This lumen is formed when a circular array of staples is used to join two pieces of tissue after which the tissue interior to the innermost circle of staples is cut out by a concentric circular retractable blade. Retraction of the circular stapler removes the cut tissue to form a lumen.

In the art of surgery, it has been known to use purse string sutures and purse string appliers for circular staplers. The suture is typically placed using a needle, staples or other suitable means for attaching the suture to the tissue. After attachment, the ends of the suture remain loose for pulling to contract or close the tissue. Conventional needles and instruments are well known in the art for inserting or attaching purse string sutures to tissue. For example, purse string surgical instruments utilizing needles and toothed jaws are disclosed in U.S. Pat. Nos. 4,345,600; 4,915,107; and 5,188,636. U.S. Pat. Nos. 4,821,939; 5,158,567; and 5,490,856 disclose purse string applicators with stapling cartridges for attaching a suture to tissue and are incorporated herein by reference in their entirety.

Surgical instruments for attaching a purse string can require a relatively high degree of dexterity. Typically, for example, at least one free unattached end portion of the suture is in a loose state, both during and after attachment to tissue. This requires the user of the surgical instrument to either hold or keep track of the unattached end portion. Furthermore, when attempting to pull the purse string to a desired tension, it can be difficult to maintain that tension while attempting other hand movements.

It would therefore be advantageous to provide a purse string instrument having means to hold or retain at least the end portion or portions of the suture during certain surgical procedures.

Additionally, with the advent of minimally invasive, e.g. endoscopic, surgical procedures, it would be advantageous to provide an endoscopic purse string device which could minimally invasively apply purse string sutures. The benefits of minimally invasive surgery, e.g. shorter recovery time, reduced patient trauma, shorter hospital stay, etc. are well known.

SUMMARY

In one aspect of the present disclosure, an endoscopic surgical stapler is provided which includes an elongated tubular member having a distal end portion and a proximal end portion, a first jaw positioned at the distal end portion of the tubular member and having a longitudinal axis, and a second jaw disposed in substantially parallel relation to the first jaw at the distal end portion of the tubular member. The second jaw is movable toward the first jaw in a direction substantially perpendicular to its longitudinal axis, while maintaining the substantially parallel relation between the first and second jaws. The surgical stapler further includes a stapling assembly disposed in each of the first and second jaws and configured to apply surgical staples to the tissue such that a suture, in combination with the surgical staples, forms a purse string with the tissue when the surgical stapler is activated.

In some embodiments, the surgical stapler includes a plunger longitudinally movable within the tubular member and a cam arm positioned to move the second jaw substantially perpendicularly to the longitudinal axis in response to longitudinal movement of the plunger.

The surgical stapler is preferably sized to allow insertion of the surgical stapler into a surgical port for use in a minimally invasive surgical procedure.

The surgical stapler can include a suture retaining member for mounting a suture onto an outer surface of the tubular member. The surgical stapler can have a plurality of guides having slots positioned on the tubular member for releasably retaining a portion of the suture adjacent the tubular member.

The first jaw can have a first length and the second jaw can have a second length, wherein the second length is greater than the first length such that the second jaw may extend proximally of the first jaw.

In some embodiments, the surgical stapler includes a locking mechanism to prevent unintended firing of the surgical staples from the surgical stapler. The locking mechanism may in some embodiments be a removable tab or a pivotable catch. The removable tab can act as a stop to limit longitudinal movement of the plunger in relation to the tubular member. The pivotable catch is preferably sized and shaped to removably couple the catch within a lock recess to limit longitudinal movement of the plunger in relation to the outer tube.

The surgical stapler can include a proximal spring to bias the plunger in a proximal position relative to the tubular member and a distal spring to bias the second jaw away from the first jaw. The proximal and distal springs can act to prevent unintentional expulsion of the surgical staples from the surgical stapler.

In another aspect of the present disclosure, an endoscopic surgical stapler is provided for applying a suture to tissue comprising an elongated tubular member having a proximal end portion and a distal end portion, and first and second jaws positioned adjacent the distal end portion of the tubular member. At least the second jaw is movable toward the first jaw from a spaced apart position to an approximated position, and each of the jaws includes a plurality of staples and a portion of a suture. An approximation mechanism moves at least the first jaw with respect to the second jaw, and includes a linear slidable member positioned within the elongated tubular member.

The biasing member may be disposed adjacent the portion of the second jaw that extends beyond the first jaw. The first jaw may be fixed, whereas the second jaw may be movable relative to the first jaw in a substantially parallel movement toward the first jaw. The first and second jaws can include anvilless stapling assemblies for forming the staples and applying a purse string.

DESCRIPTION OF THE DRAWINGS

The accompanying drawings, which are incorporated in and form part of the specification, illustrate the present disclosure when viewed with reference to the description, wherein:

FIG. 7 is a cross-sectional view of the surgical stapler of FIG. 1 taken along section line 7-7 of FIG. 1;

FIG. 8 is a cross-sectional view taken along line 8-8 of FIG. 6;

FIG. 14 is a cross-sectional view of the surgical stapler taken along section line 14-14 of FIG. 12;

FIG. 15 is a cross-sectional view of the surgical stapler taken along section line 15-15 of FIG. 13;

Figure 1:
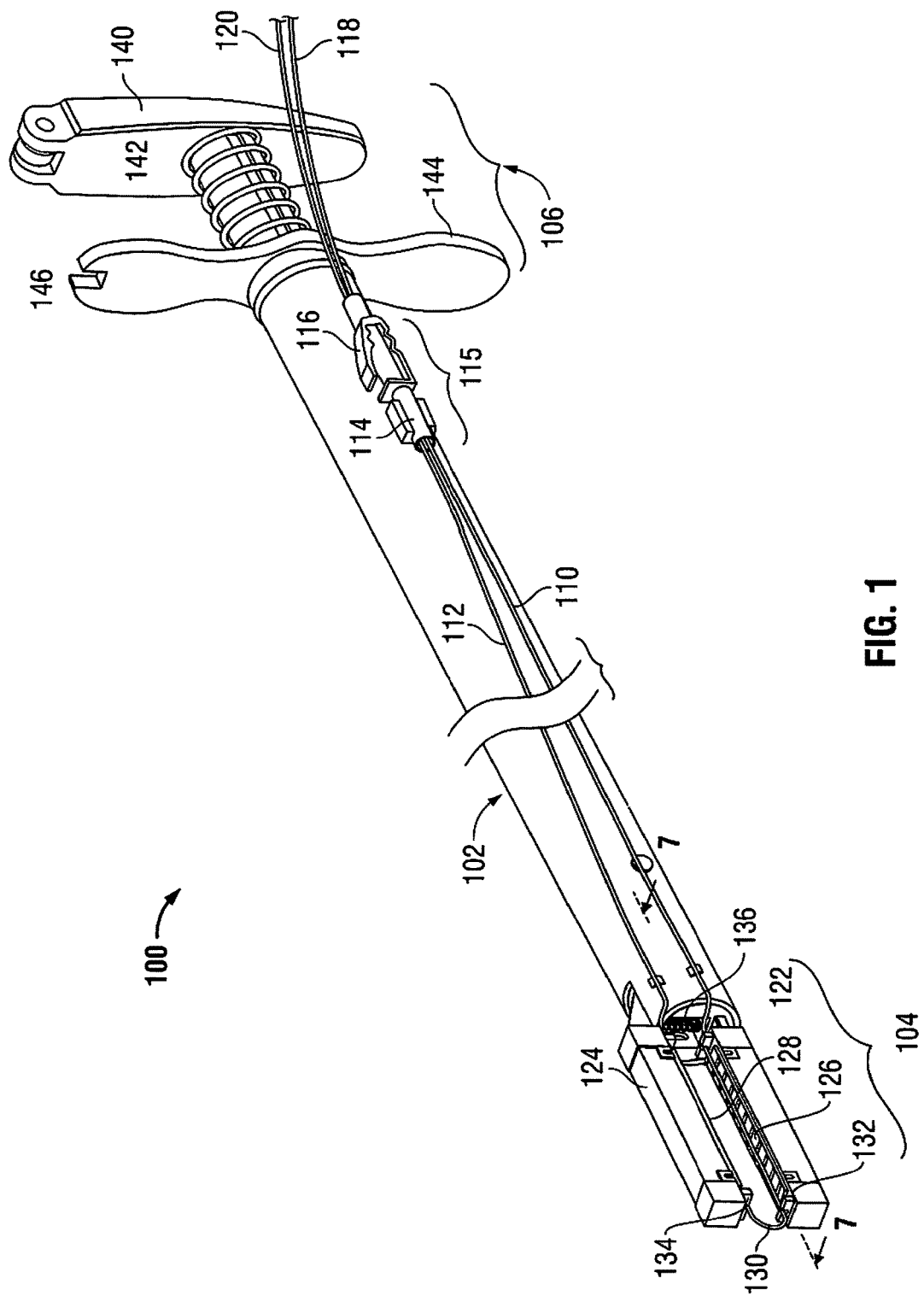
FIG. 1 is a perspective view of a surgical stapler in accordance with the present disclosure shown with the jaws in the open (spaced) position.

Other features of the present disclosure will become apparent from the following detailed description, taken in conjunction with the accompanying drawings, which illustrate, by way of example, the principles of the present disclosure.

DETAILED DESCRIPTION

Embodiments of the presently disclosed surgical stapler will now be described in detail with reference to the drawings wherein like numerals designate identical or corresponding elements in each of the several views. As is common in the art, the term "proximal" refers to that part or component closer to the user or operator, i.e., surgeon or physician, while the term "distal" refers to that part or component further away from the user. In the following description, well-known functions or constructions are not described in detail to avoid obscuring the present disclosure in unnecessary detail.

The example embodiments of the present disclosure are provided by virtue of a mechanical resecting, stapling, and/or suturing attachment which is coupleable to and remotely actuable by a mechanical device driver. In particular, the attachment includes a pair of jaws for clamping the selected section of tissue therebetween, the jaws expanding and closing in a substantially parallel disposition.

The example embodiments of the present disclosure illustrate that in a natural state, the jaws would be in an open configuration. A catch stop would be pulled back to close the jaws in order to allow for insertion of the jaws through an access port such as a trocar. Once inside the patient, the jaws would be returned to an open configuration and would be slid over tissue, where the purse string staples of the stapling assemblies would be placed. Once the surgeon determines an appropriate position, an optional safety would be removed and the surgeon would move the movable jaw toward the fixed jaw. This action causes the staples to form pinching tissue around the outer diameter of the tissue, with a suture captured inside the formed staple. The surgical device would then be withdrawn, leaving the formed staples and the suture attached to the tissue.

Prior to describing the present disclosure in further detail, it will first be helpful to define various terms that will be used throughout the following discussion. For example:

The term "connect" or "connecting" may refer to adhere, affix, anchor, attach, band, bind, bolt, bond, brace, button, cohere, fasten, couple, embed, establish, fix, grip, hold, hook, implant, link, lock, lodge, screw, seal, rivet, tack on, tighten, or unite. The terms "connect" or "connecting" may refer to linking/fastening/attaching/locking any type of materials or elements or components or units in a removable or detachable or interchangeable manner. The terms "connect" and "lock" may be used interchangeably throughout the present disclosure.

Reference will now be made in detail to embodiments of the present disclosure. While certain embodiments of the present disclosure will be described, it will be understood that it is not intended to limit the embodiments of the present disclosure to those described embodiments. To the contrary, reference to embodiments of the present disclosure is intended to cover alternatives, modifications, and equivalents as may be included within the spirit and scope of the embodiments of the present disclosure as defined by the appended claims.

Referring now in specific detail to the drawings, with like reference numerals identifying similar or identical elements, the present disclosure is shown in cooperation with a surgical stapler for applying a suture to a tissue.

With reference to FIG. 1, a perspective view of a surgical stapler in accordance with the present disclosure is presented.

The surgical stapler 100 includes a staple assembly 104 positioned at a distal end portion and a plunger assembly 106 positioned at a proximal end portion of the surgical stapler 100. A tubular member 102, forming an outer tube, extends between the distal and proximal end portions of the surgical stapler 100.

In particular, the stapling assembly 104 includes a jaw assembly. The jaw assembly includes a first jaw 122 and a second jaw 124. The first jaw 122 is preferably a stationary mounting jaw mounted to the distal end of the tubular member 102. The second jaw 124 is preferably a movable mounting jaw. In an alternative embodiment, the first jaw 122 may be of a different length compared to the second jaw 124. For example, in one embodiment, the second jaw 124 may be longer than the first jaw 122 or vice versa such that it extends proximally beyond the other jaw.

A stapling assembly 126, 128 is disposed along each of the mounting jaws 122, 124, the stapling assemblies 126, 128 being configured to apply at least one surgical staple to the tissue such that the distal end of the suture 130, in combination with the at least one surgical staple, forms a purse string with the tissue. This stapling/suturing process will be further described below with reference to FIGS. 6 and 9-13.

The stapling assembly 104 also includes a pair of suture guides 132, 134. A first guide 132 is positioned at one end of the first jaw 122 and a second guide 134 is positioned at one end of the second jaw 124. The suture guides 132, 134 are configured to receive the distal end of the suture 130. The suture 130 runs from the proximal end to the distal end of the surgical stapler 100, as will be described below.

The stapling assembly 104 also includes a biasing member 136. The biasing member 136 is for the second jaw 124 to travel linearly in a direction substantially perpendicular to its longitudinal axis, while maintaining the substantially parallel relation between the first and second jaws 122, 124. In other words, the biasing member 136 allows for the second jaw 124 to move substantially parallel to the first jaw 122.

The tubular member 102 includes a suture retaining mechanism 115. The retaining mechanism 115 is retained adjacent the tubular member 102 through which a first suture section 110 and a second suture section 112 are run. The tubular member 102 is preferably an elongated tube of deformable plastic, such as 80 Duro polyvinyl chloride. The retaining mechanism 115 releasably retains the first and second suture sections 110, 112 longitudinally along a length of the tubular member 102.

Surgical stapler 100 further includes a mounting structure for mounting the retaining mechanism 115 to the tubular member 102. For example, a holder 114 and a clamp 116 hold and clamp the first and second suture sections 110, 112 to the tubular member 102. Holder 114 is mounted adjacent the tubular member 102 and has an opening through which the suture sections extend. Clamp 116 is located proximal of holder 114, adjacent the proximal end portion of the surgical stapler 100 and positioned adjacent tubular member 102 through which first and second suture sections 110, 112 are disposed. The proximal location of clamp 116 allows a user to grasp and engage the clamp 116 during use of the surgical stapler 100, so that the proximal end 118 of the first suture section 110 and the proximal end 120 of the second suture section 112 remain intact during operation. One skilled in the art may contemplate using various combinations and equivalent embodiments of holders and clamps to releasably retain first and second suture sections 110, 112 substantially adjacent the tubular member 102. The retaining mechanism 115 can be positioned along other portions of the tubular member 102. Additionally, use of more than one retaining mechanism 115 in a plurality of different configurations is contemplated.

The proximal end portion of the surgical stapler 100 includes a plunger assembly 106. The plunger assembly 106 includes a handle 140, a spring 142, a grip 144, and a recess 146 located on a portion of the grip 144 in order to hold a catch lock 302, as described below with reference to FIG. 3. The distal spring 142 is positioned between the handle 140 and the grip 144. Upon release of the catch lock 302, the distal spring 142 moves the handle 140 away from the grip 144. The surgeon may then access and use the grip 144 to actuate the plunger assembly 106.

The guides 132, 134 may be positioned on the distal ends of the first jaw 122 and the second jaw 124, respectively. However, guides 132, 134 may alternatively in additionally be positioned on the proximal ends of the first jaw 122 and the second jaw 124, respectively. Additionally, a plurality of guides 132, 134 may be positioned across the length of the pair of stapling assemblies 126, 128, on the inner surface of the first and second jaws 122, 124.

The suture guides 132, 134 provide for running the proximal end 118 of the first suture section 110 and the proximal end 120 of the second suture section 112 through the retaining mechanism 115 located adjacent the tubular member 102, to the pair of stapling assemblies 126, 128 where the distal end of the suture 130 is located. One skilled in the art may contemplate using various combinations and equivalent embodiments of guides to releasably retain the distal end of the suture 130 substantially adjacent the first and second stapling assemblies 126, 128 of the first and second jaws 122, 124.

Moreover, during manufacture of the surgical stapler 100, suture 130 may be placed into guides 132, 134 and through tubular member 102, with suture 130 strung taut between guides 132, 134 to be disposed substantially adjacent first and second stapling assemblies 126, 128.

The movable mounting jaw or second jaw 124 includes a cam arm 202, the cam arm 202 being positioned to move the jaw 124 substantially perpendicular to the longitudinal axis in response to longitudinal movement of the plunger assembly 106 (see FIG. 1). The cam arm 202 includes a cam slot 204 for receiving a cam pin 206. The cam pin 206 allows for substantially parallel movement of the second jaw 124 relative to the longitudinal axis of the first jaw 122 and relative to the longitudinal movement of the plunger assembly 106 (see FIG. 1). Additionally, a cam block 210 (FIG. 7) having a cam surface 208 is positioned adjacent the cam arm 202. The cam block 210 is positioned at the distal end of the plunger assembly 106 and actuates the cam arm 202 to move the second jaw 124 toward the first jaw 122. That is, the distal movement of the plunger assembly 106 causes the cam surface 208 to engage cam arm 202 to cause the substantially parallel closure of the first and second jaws 122, 124 as can be appreciated by comparing FIGS. 7 and 8. The movement of the cam arm 202 also moves the second jaw 124 to apply a force against the tissue to effect firing of the staples as described below.

Figure 2:
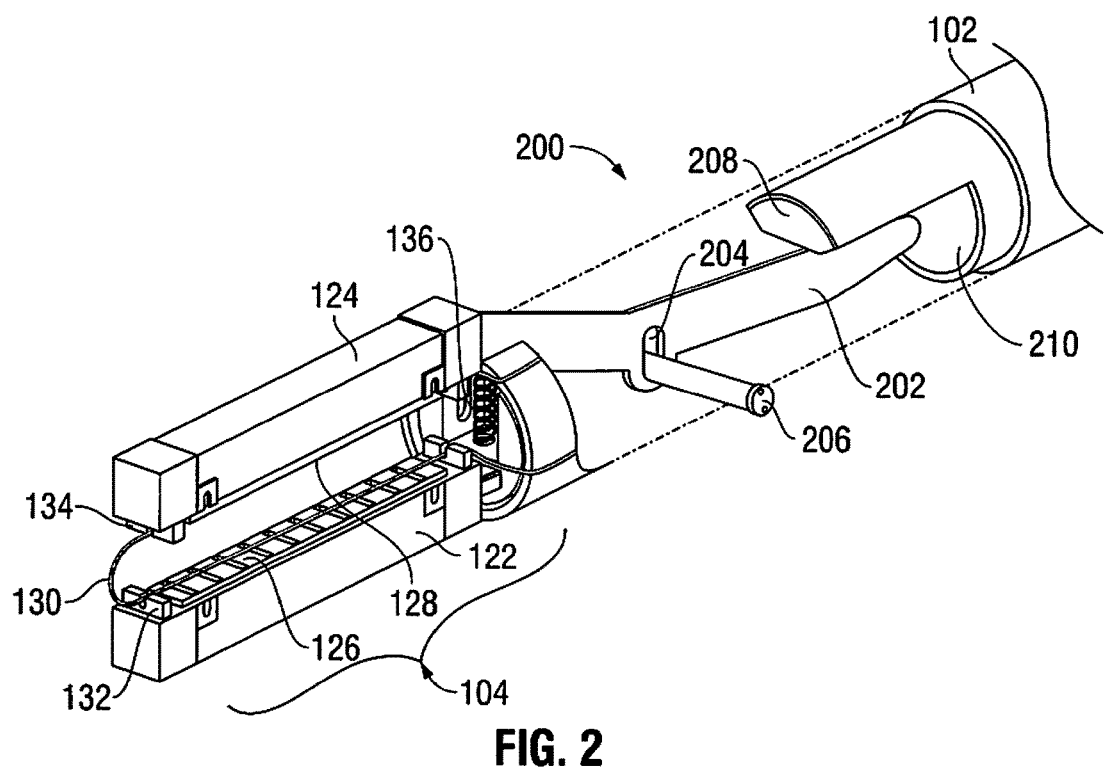
FIG. 2 is an enlarged perspective view of the distal end portion of the surgical stapler of FIG. 1, depicting the jaws in an open (spaced) position.
Figure 3:
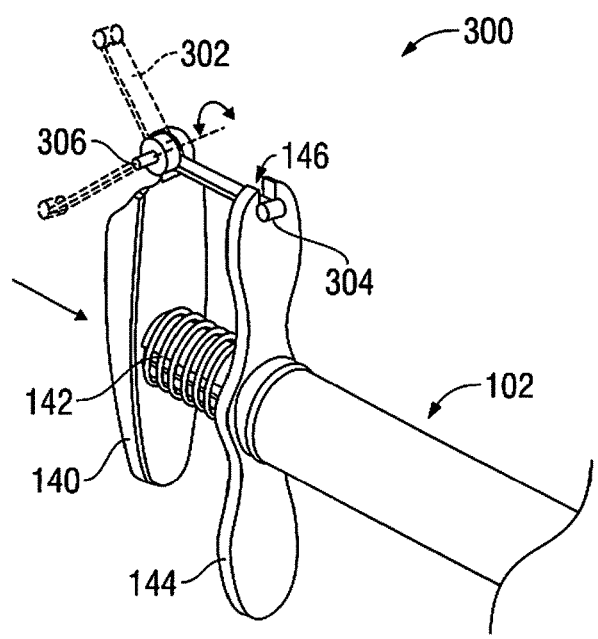
FIG. 3 is an enlarged perspective view of the proximal end portion of the surgical stapler of FIG. 1 corresponding to the jaws in a closed position.

FIG. 3 illustrates how the handle 140 and grip 144 of the plunger assembly 106 are actuated. A pivotal catch lock 302 is securely locked at the recess 146 of the grip 144. The catch lock 302 is attached to the handle 140 via a catch pin 306. The catch lock 302 is releasably secured to the grip 144 via a catch stop 304 that frictionally locks into the recess 146 of the grip 144. In operation, when the catch stop 304 is released from the recess 146 of the grip 144, i.e. pivoted out of recess 146, the handle 140 may be manipulated by a user to actuate the plunger assembly 106 to drive the cam block 210 (see FIG. 2) to engage cam arm 202, in order to move the second jaw 124 in substantially parallel movement toward the first jaw 122. It is noted that when the catch stop 304 is positioned within the recess 146, the distal spring 142 is in a compressed position. Thus, the distal spring 142 urges the handle 140 and the grip 144 apart when the catch stop 304 is released, thereby opening the first and second jaws 122, 124 in a substantially parallel manner as second jaw 124 returns to its normal position. The catch lock 302 enables the holding of the first and second jaws 122, 124 in a closed position for insertion through, for example, a surgical port 610 and surgical port tube 620 (see FIG. 6).

Figure 4:
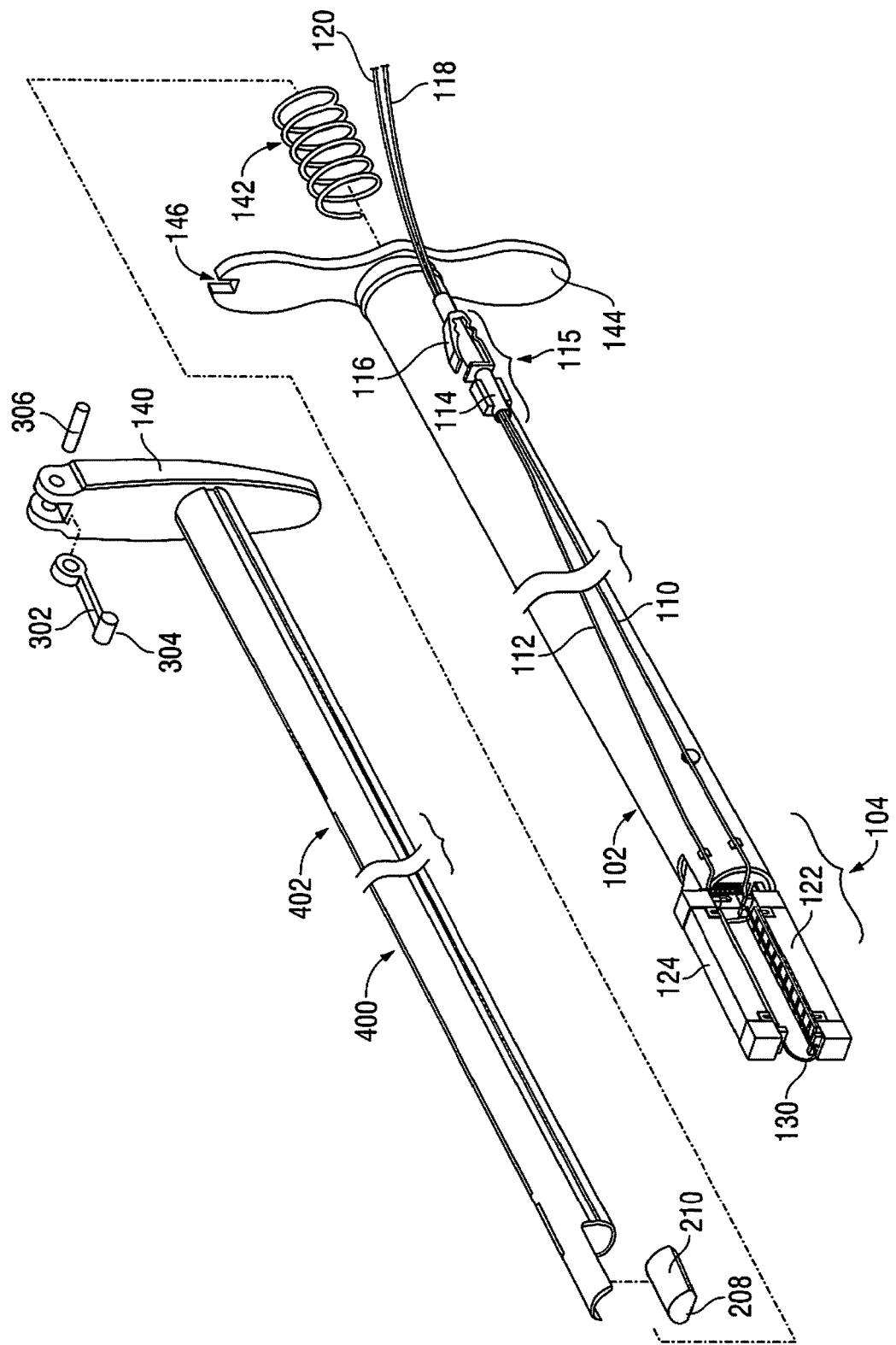
FIG. 4 is an exploded perspective view of the surgical stapler of FIG. 1 with a plunger and a proximal spring separated from an outer tube.

The exploded perspective view illustrates how certain components of the surgical instrument 100 are connected to each other; however, one skilled in the art may contemplate connecting such components in a plurality of different configurations. The handle 140 is operably connected to a proximal end of a drive shaft 402 (FIG. 4). The distal end of the drive shaft 402 includes the cam block 210 having cam surface 208 (see FIG. 2). Additionally, the catch lock 302 having a catch stop 304 is connected to an upper portion of the handle 140 via the catch pin 306 (see FIG. 3). The drive shaft 402 is slidably positioned within the tubular member 102. The drive shaft 402 travels through spring 142 in order to allow for a predetermined distance between the handle 140 and the grip 144. The remaining components have been fully described above with reference to FIGS. 1-3.

Figure 5:
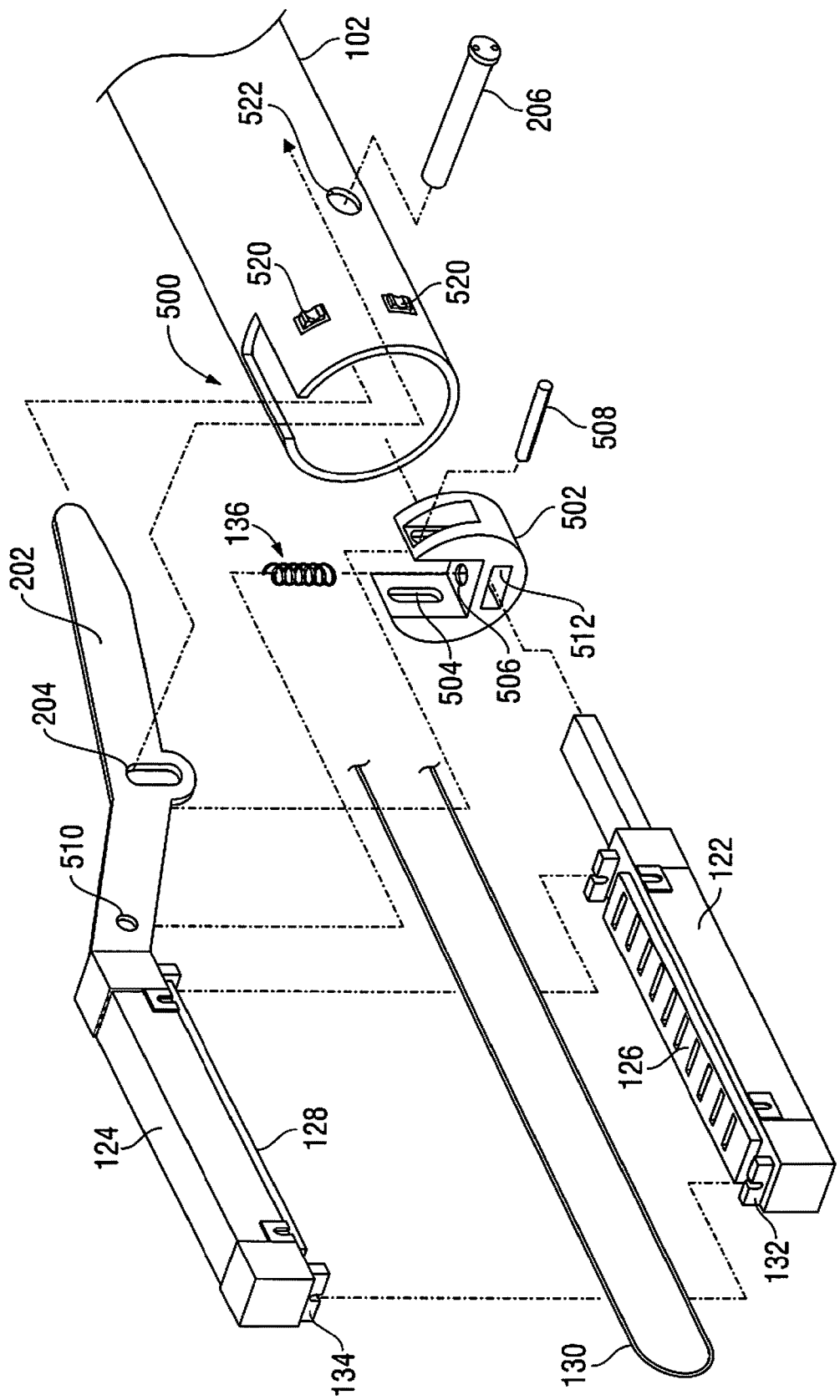
FIG. 5 is an exploded perspective view of the distal end portion of the surgical stapler of FIG. 1 with the movable mounting jaw and stationary mounting jaw separated from the outer tube.

Cam arm 202 (see FIG. 2) interconnects the second jaw 124 to the first jaw 122 via a jaw mount 502. The jaw mount 502 (FIG. 5) creates a connecting relationship between the first jaw 122, the second jaw 124, and the tubular member 102. The first jaw 122 is connected to the jaw mount 502 via a jaw receiving slot 512. The second jaw 124 is connected to the jaw mount 502 via pin 508 extending through hole 510 of cam arm 202 (FIG. 5). Biasing member 136 is inserted into the spring slot 506 of jaw mount 502. That is, a jaw mount pin 508 is inserted through the perpendicular slots 504 of the jaw mount 502 and then through the pin hole 510 in order to securedly, yet movably affix the cam arm 202 of the second jaw 124 to the jaw mount 502. This connects the first and second jaws 122, 124. The tubular member 102 connects to the cam arm 202 via the cam pin 206 inserted through a cam pin hole 522 of the tubular member 102 and engaging slot 204 of cam arm 202.

In an example embodiment, one or more tube suture guides 520 (FIG. 5) may be positioned on various regions of the outer surface of the tubular member 102 in order to provide for supplemental support of the first and second suture sections 110, 112. The guides have a recess dimensioned to frictionally engage the suture. In another example embodiment, the suture guides 520 may be positioned across the entire length of tubular member 102.

Figure 6:
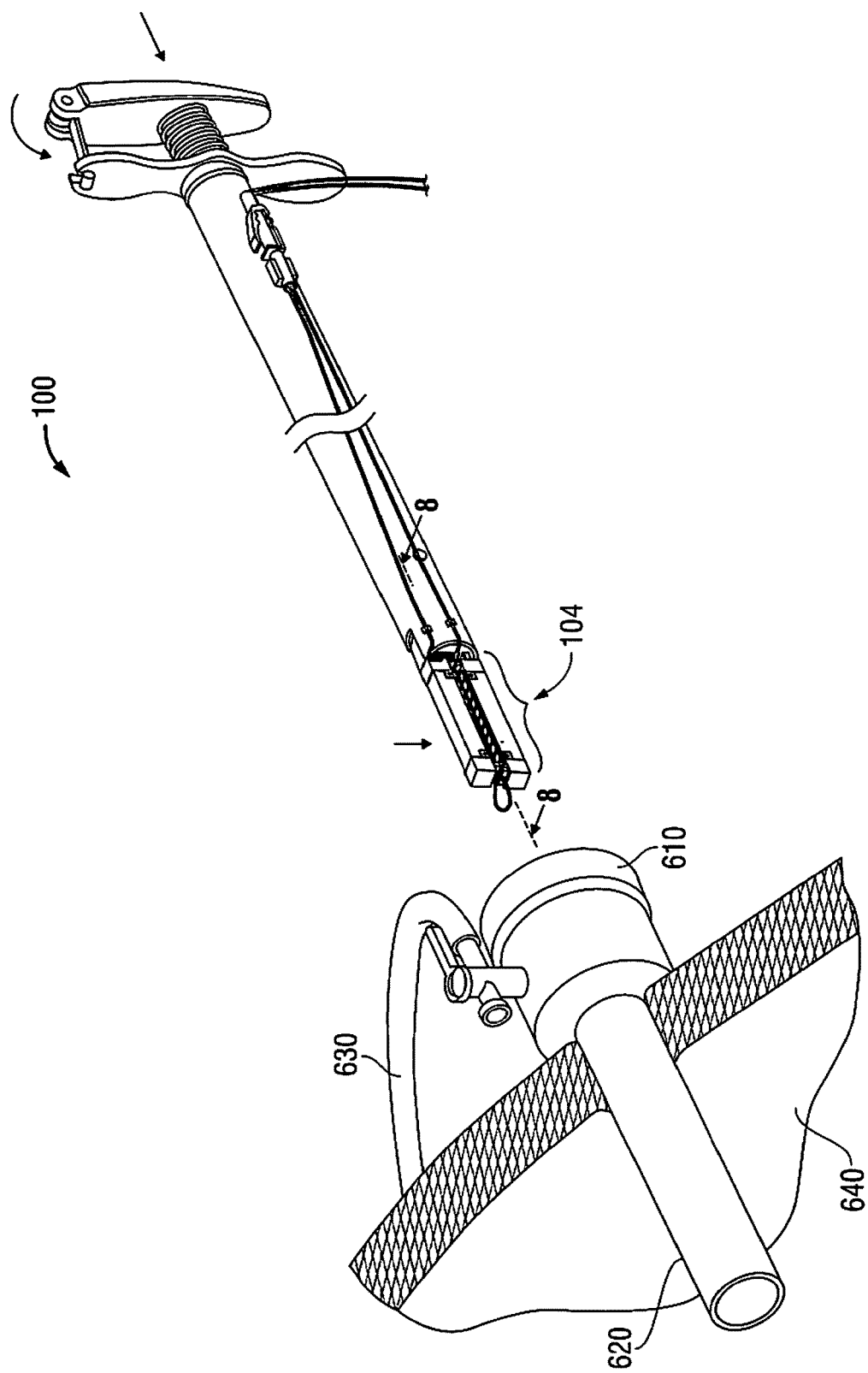
FIG. 6 is a perspective view of the surgical stapler of FIG. 1 being inserted through a surgical port and into a sub-dermal body cavity, the jaws shown in the closed position.

The view of FIG. 6 depicts the surgical instrument 100 before it is inserted into a body of a patient. The stapling assembly 104 of the surgical instrument 100 is inserted through the surgical port 610 having a surgical port tube 620. The surgical port 610 is positioned adjacent tissue 640 of a patient, and extends through the tissue 640 of the patient to provide access to the body cavity of the patient. One or more connectors 630 may be connected to the surgical port 610. For certain applications, the surgical port can include one or more internal seals.

The operation of the surgical stapler 100 will be described with reference to FIGS. 6 and 9-13. In the illustrated embodiment, in summary, in a natural state, the jaws would be in an open configuration. The jaws would then be closed to allow for insertion of the jaws through a surgical port, e.g. trocar. (Catch lock 302 can be used to hold the jaws in the closed position). Once inside the patient, the jaws would be returned to an open configuration and would be slid over tissue, where the purse string staples of the stapling assemblies would be placed. Once the surgeon determines an appropriate position, plunger would be actuated to move the movable jaw toward the fixed jaw. On continued movement, the staples would be forced from the jaws, causing the staples to form pinching tissue around the outer diameter of the tissue, with a suture captured inside the formed staple. Afterward, the plunger would be released, allowing the jaws to move to the open position, thus leaving the formed staples and the suture attached to the tissue. The jaws would then be re-closed for removal through the port. A two stage operation is therefore contemplated with the first stage closing the jaws to clamp tissue and the second stage applying sufficient force to the tissue to retract elements within the jaws as described below to form the staples. Note a tactile indicator, or a stop, can be provided to demarcate the two stages. If a stop is provided, it would be released after initial jaw approximation to allow additional movement to fire the staples.

It is also contemplated that alternatively the jaws can be in a closed position in a natural state and then after insertion through a surgical port moved to an open position to be slid over tissue.

Figure 9:
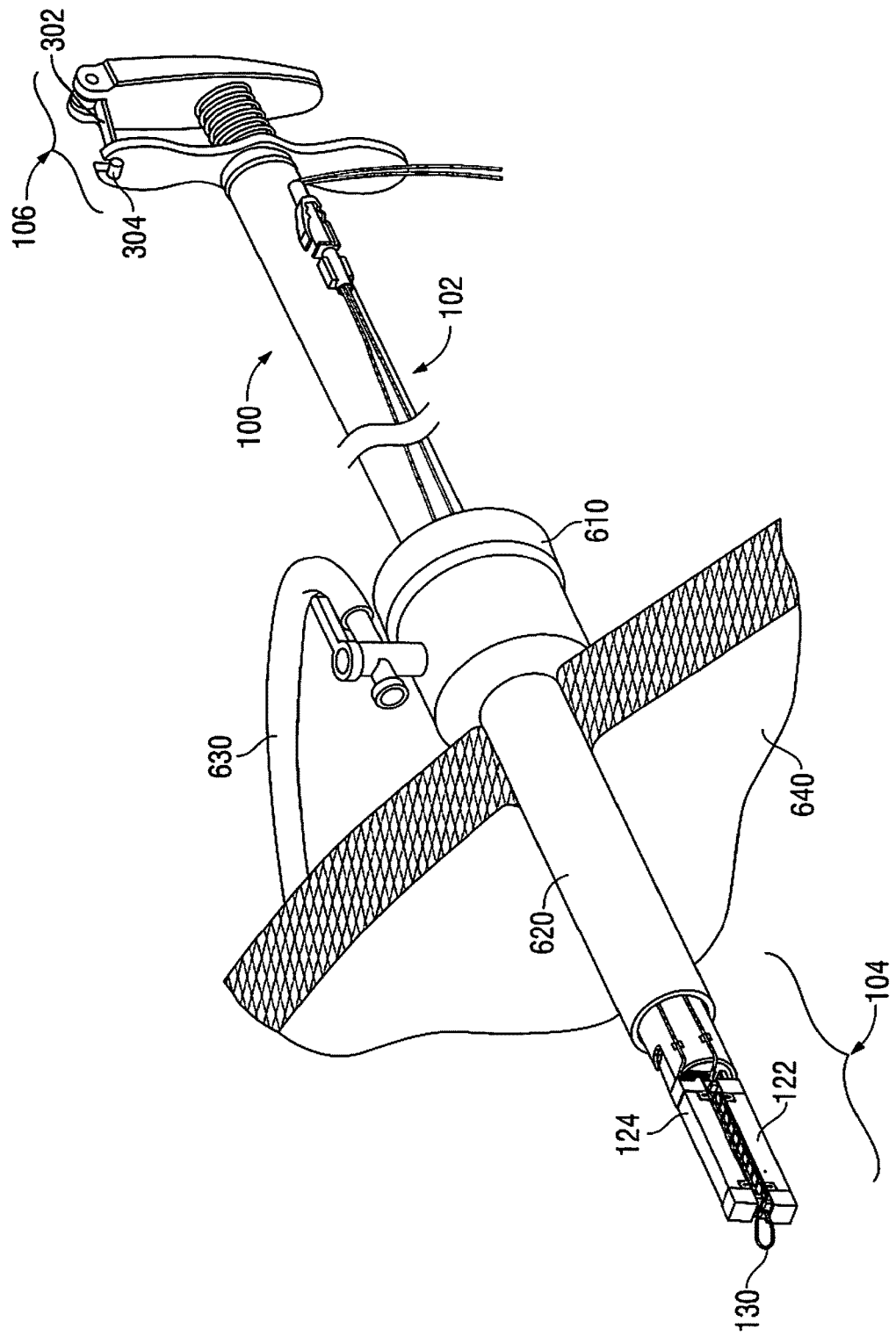
FIG. 9 is a perspective view of the surgical stapler of FIG. 1 located within and extending through the surgical port and into a sub-dermal body cavity, showing the jaws in the closed position.

In use, and with initial reference to FIG. 9, in a first position, a portion of the surgical instrument 100 is inserted through the surgical port 610 and the surgical port tube 620 so as to expose the stapling assembly 104 within the body of the patient. In the first position of FIG. 9, the plunger assembly 106 remains in a locked configuration due to the locking engagement of the catch stop 304 of catch lock 302 in recess 146 of the grip 144 (see also FIG. 3).

Figure 10:
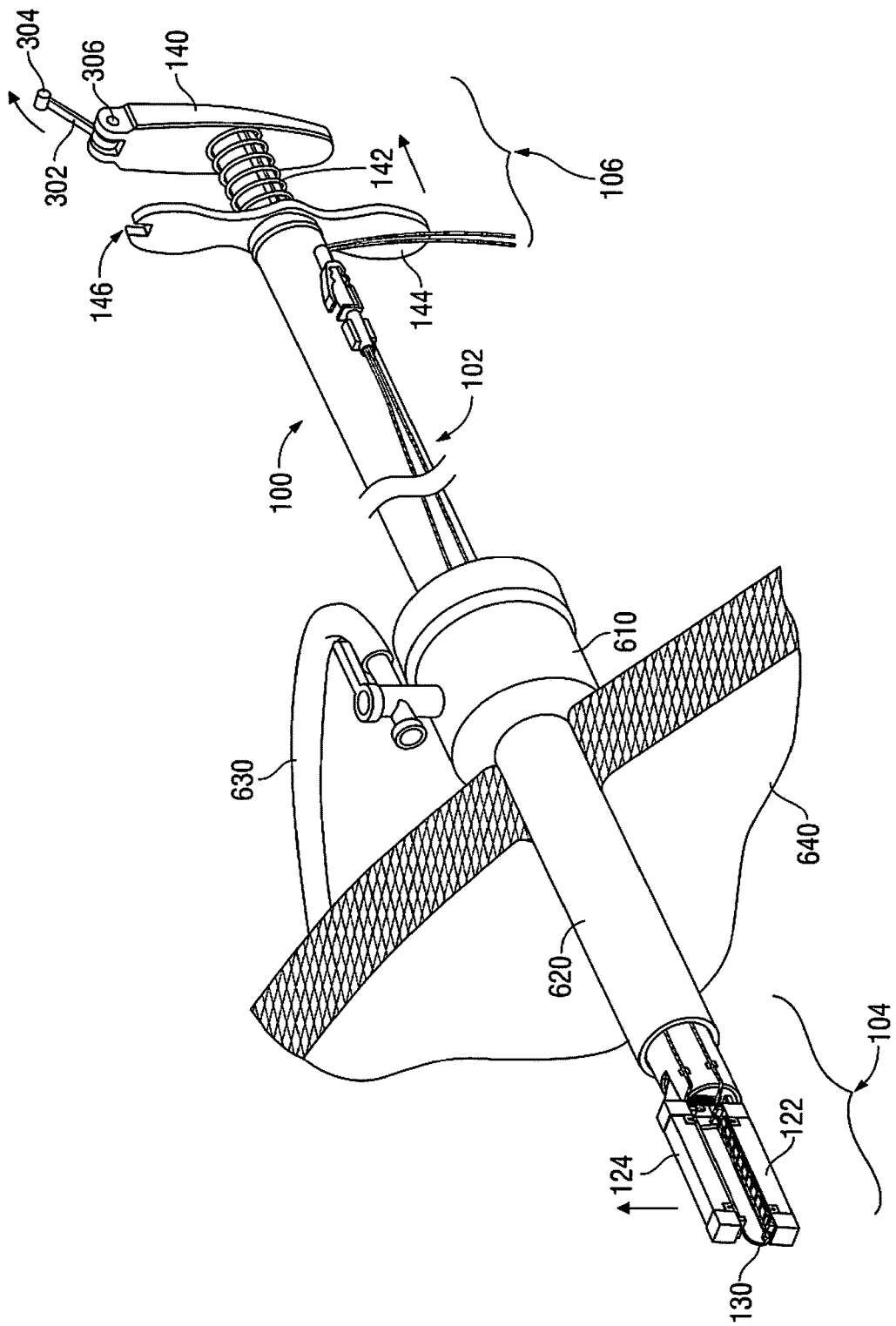
FIG. 10 is a perspective view of the surgical stapler of FIG. 1 inserted through a surgical port to apply purse string sutures to sub-dermal tissue, showing the jaws in the open position.

Next, as shown in FIG. 10, in a second position, the catch stop 304 of the catch lock 302 is manually released by the surgeon from the recess 146 of the grip 144 in order to actuate the plunger assembly 106 via the distal spring 142 (see also FIG. 3). That is, when the catch stop 304 is released, the handle 140 of plunger assembly 106 is moved proximally in a longitudinal direction due to the bias of spring 142. This withdraws the cam block 210 from cam arm 202 (see FIG. 2) so that the second jaw 124 moves away from the first jaw 122 in a substantially parallel fashion (see also the open jaw position of FIG. 7). Thus, an opening is created between the first and second jaws 122, 124 in order to grasp tissue, for example, intestinal tissue 1110 (see FIGS. 11-13 described below).

Figure 11:
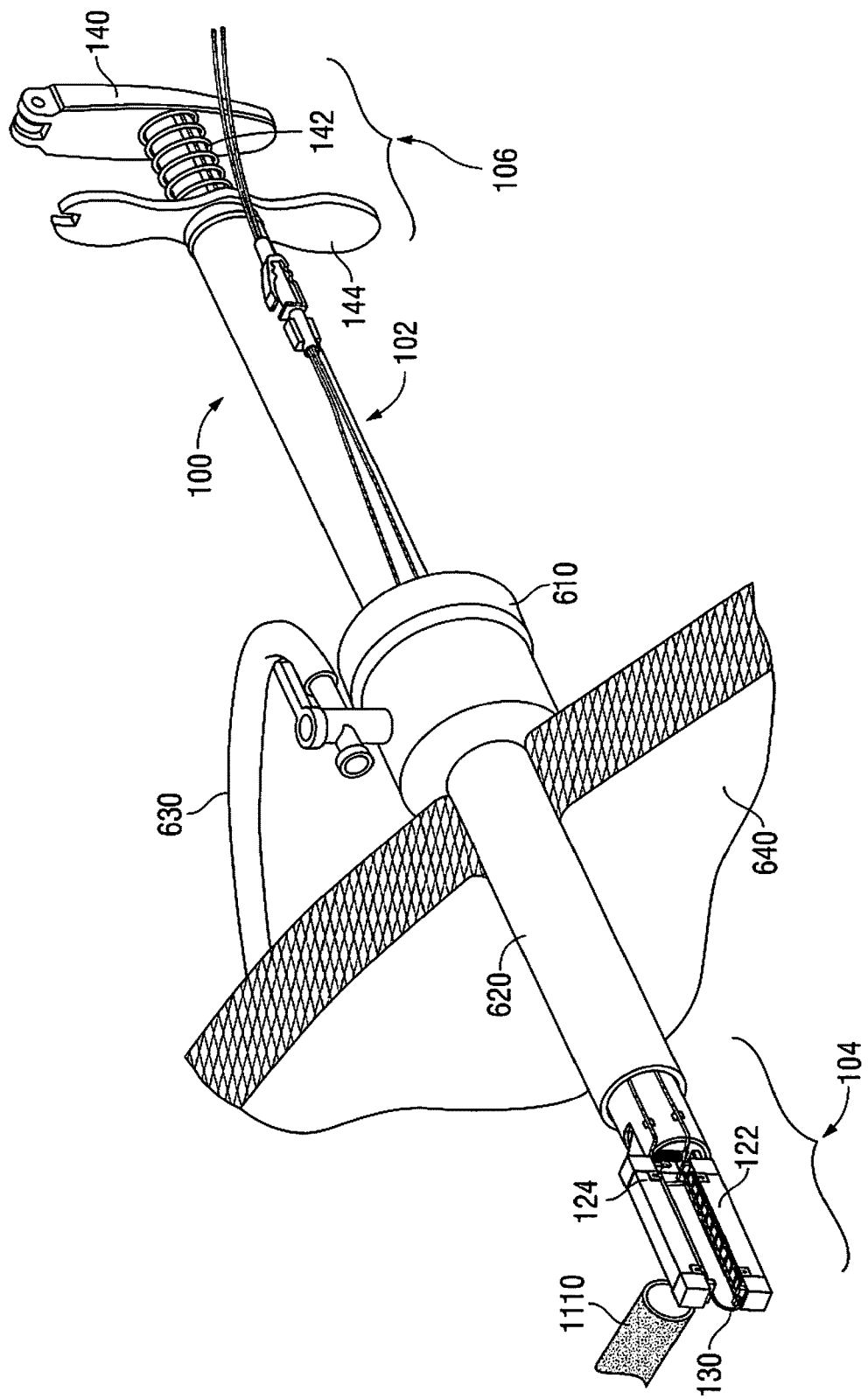
FIG. 11 is a perspective view of the surgical stapler of FIG. 1 inserted through a surgical port and with a tissue section being inserted between the jaws of the surgical stapler.

The first and second jaws 122, 124 are moved to approach a target as shown in FIG. 11, such as, for example, intestinal tissue 1110. Once the surgeon locates the target tissue 1110, the surgeon may maneuver the first and second jaws 122, 124 to grasp the target tissue 1110.

Figure 12:
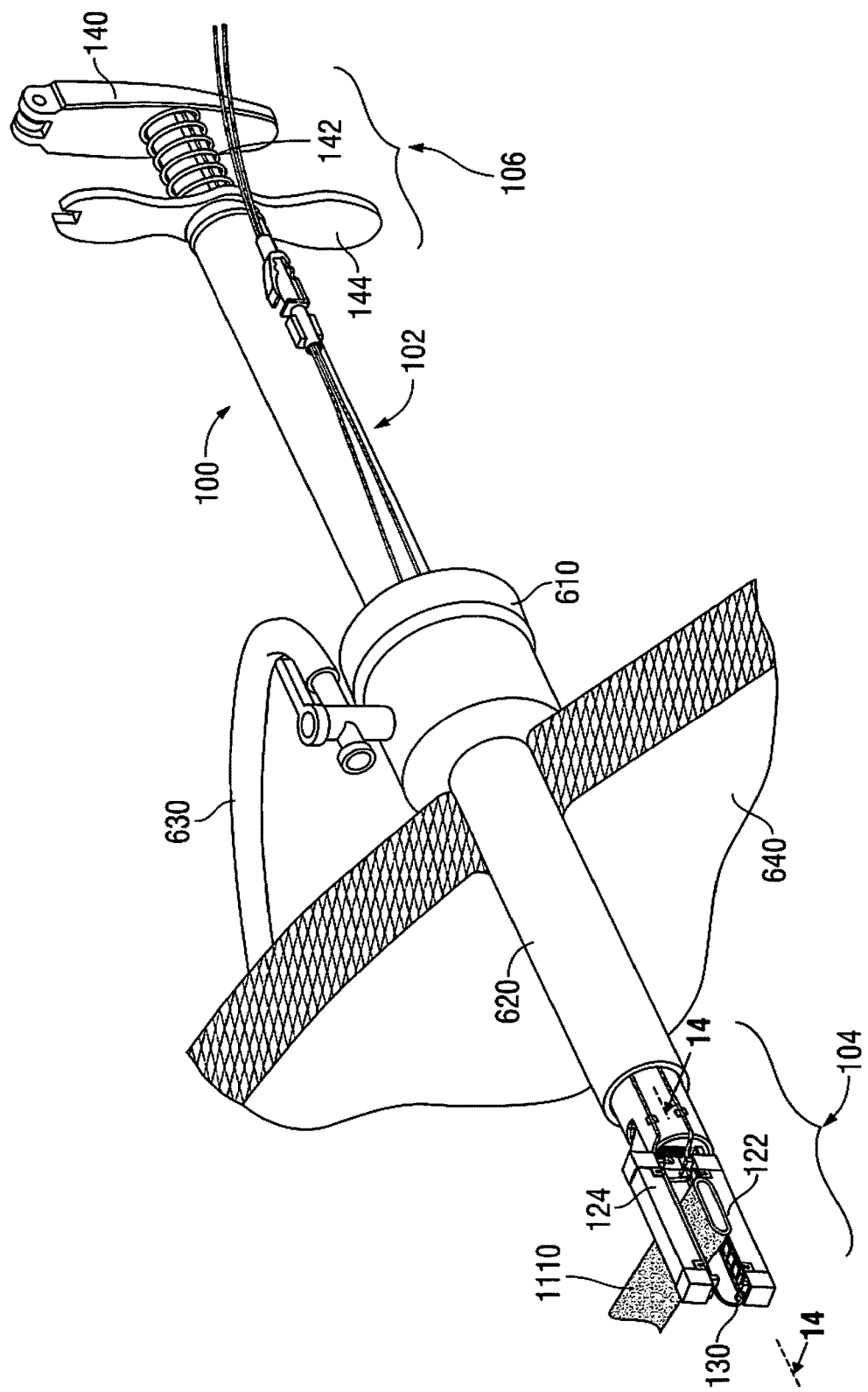
FIG. 12 is a perspective view of the surgical stapler of FIG. 1 inserted through a surgical port and the tissue section located between the jaws of the surgical stapler.
Figure 13:
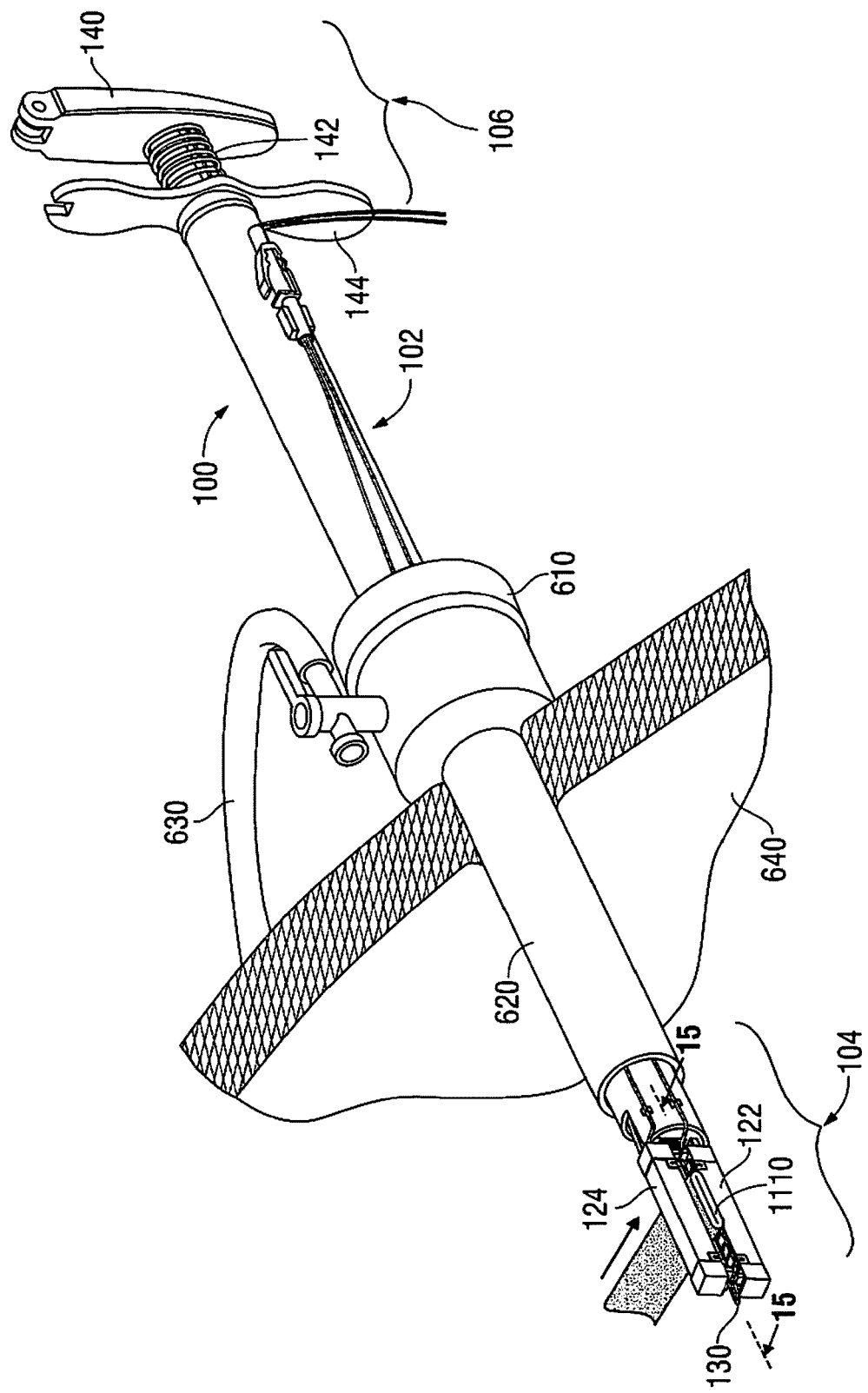
FIG. 13 is a perspective view of the surgical stapler of FIG. 1 inserted through a surgical port, wherein the surgical stapler is applying the purse string suture to the tissue section.

The first and second jaws 122, 124 then grasp a portion of the intestinal tissue 1110 as shown in FIG. 12 (and FIG. 14). The intestinal tissue 1110 is positioned between the first and second jaws 122, 124 so that the first and second stapling assemblies 126, 128 contact a portion or portions of the tissue 1110. The cam arm 202 can be partially moved downwardly by initial longitudinal movement of the plunger assembly 106 so as to partially compress the biasing member 136. This is shown by the movement of the cam slot 204 relative to the fixed cam pin 206. The cam slot 204 may move within a predetermined region defined by the location of the cam pin 206.

The surgeon subsequently manipulates the handle 140, e.g. moves the handle 140 longitudinally distally to overcome the bias of spring 142 in order to actuate the plunger assembly 106 to move the cam block 210 to the cam arm 202 (see FIG. 2), which in turn moves the second jaw 124 closer to the first jaw 122 in a substantially parallel fashion. That is, as the cam block 210 moves distally, the cam surface 208 rides across the top surface of the cam arm 202 to force/actuate the second jaw 124 to move in substantially parallel movement relative to the first jaw 122. This overrides the distal spring 136 which normally maintains the jaws 122, 124 open relative to each other. By moving the second jaw 124 closer to the first jaw 122 in a substantially parallel fashion, the intestinal tissue 1110 is firmly grasped between the first jaw 122 and the second jaw 124 (see also FIG. 15). The firm grasp allows the first and second stapling assemblies 126, 128 to firmly contact the tissue 1110 in order to fire staples through the tissue 1110 and/or to suture the tissue 1110 in order to form a purse string suture. Note that the cam arm 202 is fully moved downwardly so as to fully compress the biasing member 136. (One skilled in the art may contemplate using a plurality of different biasing members to interact with the cam arm 202). This is shown by the movement of the cam slot 204 relative to the fixed cam pin 206. The cam slot 204 may move within a predetermined region defined by the location of the cam pin 206. Therefore, in accordance with FIGS. 14 and 15, the second jaw 124 is movable relative to the first jaw 122, in a substantially parallel manner, via a cam arm 202 riding in a cam slot 204. Moreover, in FIG. 14, the distal end of the suture 130 is somewhat taut, whereas in FIG. 15, the distal end of the suture 130 is loose.

Figure 17:
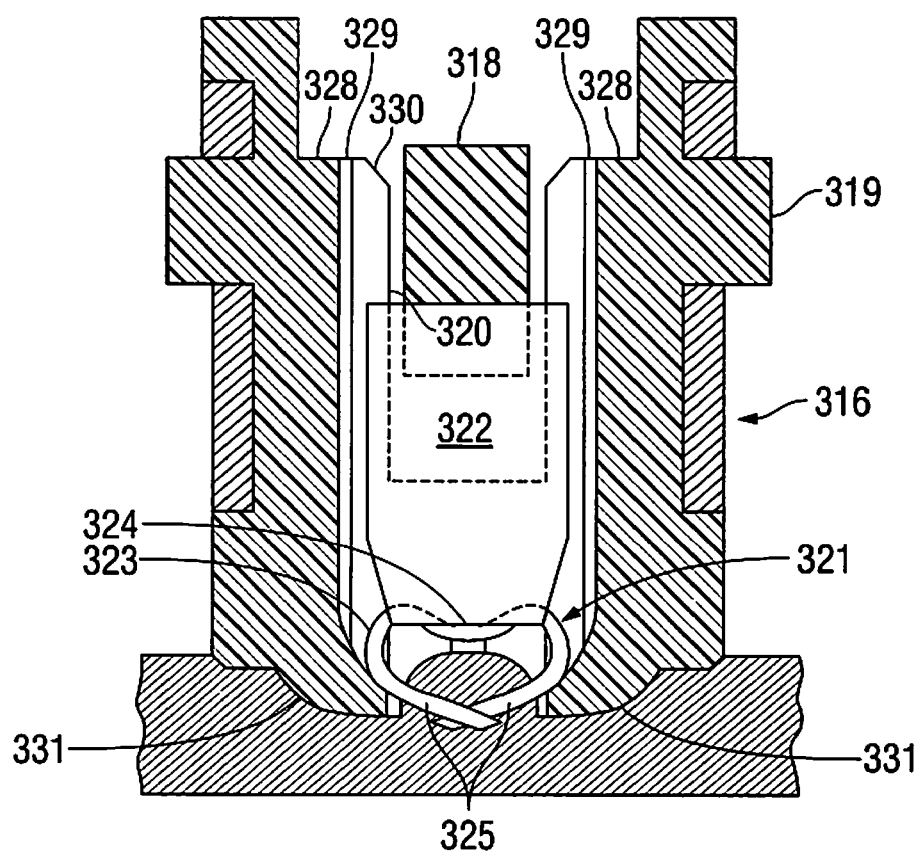
FIG. 17 is a cross-sectional view illustrating formation of a staple of the surgical stapler of FIG. 1.

The staples are formed by anvilless stapling assemblies as shown in FIG. 17. Staple cartridge 316 has a housing 319 having a pair of opposed walls 328, each defining an internal opening 320. In addition, each wall 328 is provided on the outside with a stiffener plate and has a first slot 329 extending longitudinally of the opening 320 in order to slidingly receive one side of a staple 321, that is, a rounded transition portion. In addition a second slot 330 of greater width than the slot 329 extends coaxially of the slot 329 in order to slidably receive one side of a former 322. Former 322 is moved by rib 318.

The width of a staple 321 is greater than the width of a pusher 322. Further, the lower surface of each former 322 is provided with a surface complementary to the undulating base 323 of a staple 321 so as to have a projection (not shown) seated in the recess 324 of the staple 321. This arrangement serves to center the staple 321 within the opening 320 while also ensuring uniform motion of a staple 321 out of the opening 320.

The legs 325 of staple 321 are deformed at the mouth of each opening 320 by a pair of inwardly directed lips 331. As indicated, each lip 331 is disposed at one end of the staple receiving slot 329 in a wall 328. Further, the lips 331 are spaced apart to define an outlet of less width than the opening 320 and less width than a staple 321.

Thus, as jaws apply pressure to tissue, the lips 331 are pushed rearwardly while former 322 remains stationary applying lateral forces against the legs 325 by the lips 331 so that the legs 325 begin to deform and move towards each other while penetrating into the layer of tissue.

As the staple is formed, the biasing force on the former 322 is sufficient to push the deformed staple 321 through the outlet of the mouth of the opening 320 past the lips 331 while deforming the lips 331 sufficiently to permit passage. The amount of deformation of the lips 331 is sufficient to permit passage of the deformed staple 321 while at the same time being insufficient to overly compress the layer of tissue.

Once the stapler has been fired, the purse string is pulled from the retainers and the stapler removed from the body.

In summary, with reference to FIGS. 6 and 9-13 the plunger assembly 106 operably cooperates with the cam arm 202, where the cam arm 202 slidably moves within a predetermined space defined by a cam slot 204. The cam slot 204 moves and the biasing member 136 compresses substantially perpendicular to a longitudinal axis of the stapler. Furthermore, the perpendicular slot 504 of the jaw mount 502 may be moved in relation to the movement of the cam arm 202. The perpendicular slot 504 is configured to move within a region defined by a fixed jaw mount pin 508.

Figure 16:
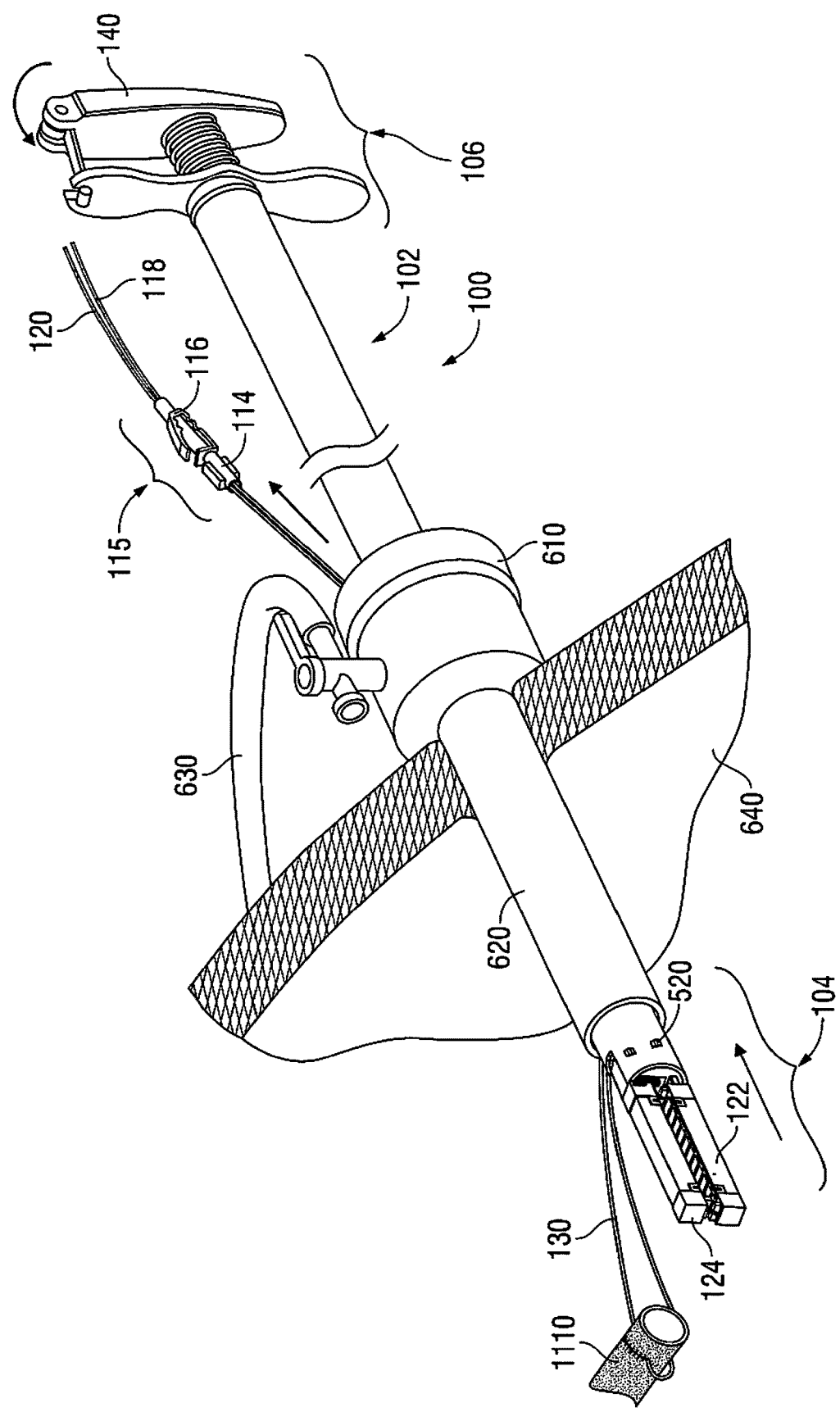
FIG. 16 is a perspective view of the surgical stapler of FIG. 1 inserted through a surgical port with the purse string suture attached to the lumen and the suture separated from the surgical stapler.

In FIG. 16, the stapling assembly 104 has completed its task by stapling/suturing the target tissue 1110. The staples can be applied in the manner described in U.S. Pat. No. 4,821,939, incorporated by reference herein in its entirety. The distal end of the suture 130 is suspended from the target tissue 1110. The suture 130 may be released from the surgical stapler 100 by the clamp 116. The clamp 116 may be released from the holder 114 in order to allow the surgeon to cut the suture 130.

In an alternative embodiment, one skilled in the art may contemplate making the first jaw movable and the second jaw fixed, by connecting the cam arm to the first jaw, instead of the second jaw. It is also contemplated that both jaws may each include a cam arm in order to make both jaws movable. In each of these scenarios, the jaws will move in a substantially parallel fashion relative to each other. It is also contemplated that one or both of the jaws can move in a pivoting movement.

In an alternative embodiment, a safety mechanism (not shown) may be provided at the proximal end of handle 140 for preventing undesired clamping of the handle 140. Safety mechanism may be in the form of a lever pivotally mounted about a pivot such as a pin. The safety mechanism may be sized to permit pivoting by a thumb or a free finger of the user.

In an alternative embodiment, the tubular member 102 may be a flexible shaft. The flexible shaft may include a tubular sheath formed of an elastomeric material. Various lengths of this shaft may be provided in conjunction with the present disclosure. Moreover, the flexible shaft 102 and the plunger assembly 106 may be separable. If separable, the interface between the proximal end of the shaft 102 and the distal end of the handle 140 should include a coupling means for any drive components. In alternate embodiments, the flexible drive shaft 102 can be capable of translating a torque from one or more motors in the handle 140 to the distal end of the shaft 102, while still being flexible enough to be bent, angled, curved, etc. as the surgeon deems necessary to "snake" through the bowel of a patient. One skilled in the art may contemplate a handle that includes no motors, or any other type of electro-mechanical driving means.

In an alternative embodiment, the handle 140 may include a remote status indicator (not shown). The remote status indicator may comprise an LCD (or similar read output device) by which the user may gain knowledge of the position of components (for example whether a clamping element is in the proper position prior to the driving of the staples).

In an alternative embodiment, the first and second stapling assemblies 126, 128 may each include a plurality of sensors (not shown). The first stapling assembly 126 may include a first sensor electrode that electrically communicates via communication wires with a first contact pad, and the second stapling assembly 128 may include a second sensor that electrically communicates via communication wires with a second contact pad. The contact nodes may electrically communicate with communication wires to form a sensor circuit, such that when the first jaw 122 and the second jaw 124 are clamped together, the sensor electrodes are in contact, the sensor circuit is closed, and the surgeon is alerted via other circuit components (not shown) to the clamped position of the jaws 122, 124.

Suture material may be classified as either absorbable or non-absorbable. Absorbable suture may be placed below the skin surface where in time, the body decomposes, dissolves, and absorbs the suture material. There are numerous non-absorbable suture materials also used during surgical procedures. The non-absorbable materials may be employed and manually removed after the intended purpose has been completed such as a surgical site that is considered healed.

While the present disclosure has been particularly shown and described with reference to the preferred embodiments, it will be understood by those skilled in the art that various modifications inform and detail may be made therein without departing from the scope and spirit of the present disclosure. Accordingly, modifications such as those suggested above, but not limited thereto, are considered the scope of the present disclosure.

The invention claimed is:

1. An endoscopic surgical stapler for applying a suture to tissue comprising:
   an elongated tubular member having a proximal end and a distal end;
   first and second jaws positioned adjacent the distal end of the elongated tubular member and movable relative to one another between spaced apart position and an approximated position, each of the jaws including a plurality of staples and a portion of the suture; and
   a suture retaining member for mounting the suture along the elongated tubular member.

2. The surgical stapler of claim 1, wherein the suture retaining member is positioned proximal to the distal end of the elongated tubular member.

3. The surgical stapler of claim 1, further comprising a second suture retaining member positioned proximal to the suture retaining member.

4. The surgical stapler of claim 1, wherein the suture is supported on an outer surface of the elongated tubular member.

5. The surgical stapler of claim 1, wherein the suture retaining member defines a slot defined in an outer surface of the elongated tubular member.

6. The surgical stapler of claim 1, further comprising a clamp releasably mounted to the elongated tubular member adjacent the proximal end of the elongated tubular member, the clamp holding first and second segments of the suture.

7. The surgical stapler of claim 6, wherein the portions of the suture within the jaws are between the first and second segments of the suture.

8. The surgical stapler of claim 1, wherein the first jaw has a first length and the second jaw has a second length greater than the first length.

9. The surgical stapler of claim 1, wherein the elongated tubular member is flexible along a longitudinal axis thereof.

10. The surgical stapler of claim 9, further comprising a spring operatively associated with the plunger, the spring being configured to bias the plunger towards a proximal position relative to the elongated tubular member.

11. The surgical stapler of claim 9, wherein the plunger has a proximal position in which the jaws are in the spaced apart position, and a distal position in which the jaws are in the approximated position.

12. The surgical stapler of claim 11, wherein the safety mechanism is a removable tab that acts to limit longitudinal movement of the plunger in relation to the elongated tubular member.

13. The surgical stapler of claim 11, wherein the elongated tubular member includes a proximal flange at the proximal end thereof defining a lock recess, and wherein the safety mechanism is a pivotable catch that is sized and shaped to removably couple with the lock recess to limit longitudinal movement of the plunger in relation to the elongated tubular member.

14. The surgical stapler of claim 9, further comprising a safety mechanism for preventing unintended movement of the first and second jaws towards the approximated position.

15. The surgical stapler of claim 1, further comprising a plunger longitudinally movable in relation to the elongated tubular member to move the jaws between the spaced apart and approximated positions.

16. The surgical stapler of claim 1, wherein the first jaw or the second jaw includes an anvilless stapling assembly for forming the staples and applying a purse string with the suture.

17. The surgical stapler of claim 16, wherein the anvilless stapling assembly includes a housing and a former, the former configured to move towards a tissue contacting surface of the first jaw or the second jaw to form the plurality of staples.

18. The surgical stapler of claim 17, wherein the former is configured to engage the plurality of staples to fire the plurality of staples through the tissue contacting surface of the anvilless stapling assembly.

19. The surgical stapler of claim 18, wherein the housing includes lips adjacent the tissue contacting surface that are configured to deform first and second legs of the plurality of staples towards one another as the former fires the plurality of staples through the tissue contacting surface.

* * * * *